United States Patent [19]

Schulz et al.

[11] Patent Number: 5,474,917
[45] Date of Patent: Dec. 12, 1995

[54] MODIFIED CYCLODEXTRIN GLYCOSYLTRANSFERASES FOR PRODUCING γ-CYCLODEXTRINS

[75] Inventors: Georg E. Schulz, Denzlingen; Anton Candussio, Munich, both of Germany

[73] Assignee: Consortium für elektrochemische Industrie GmbH, Munich, Germany

[21] Appl. No.: 263,764

[22] Filed: Jun. 22, 1994

[30] Foreign Application Priority Data

Jun. 24, 1993 [DE] Germany ............................ 43 21 047.3
Jul. 22, 1993 [DE] Germany ............................ 43 24 650.8

[51] Int. Cl.$^6$ ............................ C12N 9/10; C12N 15/54; C12P 19/18
[52] U.S. Cl. ............................ 435/97; 435/193; 536/23.2; 935/10; 935/14
[58] Field of Search ............................ 435/193, 97; 935/10, 935/14; 536/23.2

[56] References Cited

U.S. PATENT DOCUMENTS

| | | | |
|---|---|---|---|
| 3,812,011 | 5/1974 | Okada et al. | 435/97 |
| 4,418,144 | 11/1983 | Okada et al. | 435/96 |
| 4,808,232 | 2/1989 | Beesley | 127/46.3 |
| 4,822,874 | 4/1989 | Schmid et al. | 536/102 |

FOREIGN PATENT DOCUMENTS

| | | |
|---|---|---|
| 0017242 | 10/1980 | European Pat. Off. . |
| 49124285 | 11/1974 | Japan . |
| 62-25976 | 2/1987 | Japan . |
| 03053892 | 3/1991 | Japan . |
| 2169902 | 7/1986 | United Kingdom . |
| 9114770 | 10/1991 | WIPO . |

OTHER PUBLICATIONS

Database WPI, Week 8813, Derwent Publications Ltd., London, GB; AN 88–088335 & JP–A–63039597 (Hayashibara Biochem), Feb. 20, 1988 (abstract).
Applied and Environmental Microbiology, vol. 58, No. 12, Dec. 1992, Am. Soc. Microbiol., Washington, D.C., US; pp. 4016–4025 S. Fujiwara et al. "Cyclization characteristics of cyclodextrin glucanotransferase are conferred by the NH2–terminal region of the enzyme", FIG. 3,7.
Agric. Biol. Chem., vol. 54, No. 1, Jan. 1990, Tokyo, Japan, pp. 197–201, T. Kaneko et al., "Comparison of CD composition produced by chimeric CGTases".
Biotechn. Appl. Biochem., vol. 12, No. 4, Aug. 1990, Academic Press, N.Y., US, pp. 387–396, J. Hellman et al. "Effects of modifications at the C–terminus of cyclomaltodextrin glucanotransferase from *Bacillus circulans* var. alkalophilus on catalytic activity".
Database WPI, Week 9313, Derwent Publications Ltd., London, GB: AN 93–103608, & JP–A–5041985 (Oji Corn Starch Co. Ltd.), Feb. 23, 1993. (abstract).
Database WPi, Week 9151, Derwent Publications Ltd., London, GB, AN 91–373420, & JP–A–3251183 (Oji Corn Starch KK) 8. Nov. 1991. (abstract).
Biochemistry, vol. 31, No. 37, Sep. 22, 1992, Am. Chem. Soc. Washington, D.C., US, pp. 8740–8746, C. Klein et al.

"Catalytic center of cyclodextrin glycosyltransferase derived from X–ray structure analysis combined with site directed mutagenesis".
J. Fermentation and Bioengineering, vol. 74, No. 6, 1992, Suita, Japan; pp. 345 to 351, N. Kitamoto et al. "Cloning and sequencing glucanotransferase from *Bacillus* sp. KC201".
Database WPI, Week 9339, Derwent Publications Ltd., London, GB, AN 93–308317 & JP–A–5219948 (Uozumi T) Aug. 31, 1993 (abstract).
Journal of Biotechnology, vol. 32, No. 3, 1994, Elsevier, Amsterdam, NL, pp. 283–288, K.–A. Sin et al. "Replacement of an amino acid residue of cyclodextrin glucanotransferase of *Bacillus ohbensis* doubles the production of gamma–cyclodextrin".
Database WPI, Week 9344, Derwent Publications Ltd., London, GB; AN 93–347473 & JP–A–5244945 (Nippon Shokuhin Kako KK), Sep. 24, 1993 (abstract).
J. Bacteriol. (1986) 166, pp. 1118–1122, Toshiya Takano et al. "Molecular Cloning, DNA–Nucleotide Sequencing, and Expression in *Bacillus subtilis* Cells of the *Bacillus macerans* Cyclodextrin Glucanotransferase Gene" is an English language reference.
Gene (1986) 47, pp. 269–277, Florian Binder, O. Huber and August Böck, "Cyclodextrin–glycosyltransferase from *Klebsiella pneumoniae* M5al: cloning, nucleotide sequence and expression" is an English language reference.
Appl. Microbiol. Biotechnol. (1990) 34, pp. 229–230, Hans Bender, "Highly homologous cyclodextrin glycosyltransferases from *Bacillus circulans* strain 8 and a strain of *Bacillus licheniformis*" is an English language reference.
Journal of General Microbiol. (1988) 134, pp. 97–105, Takahiro Kaneko et al. "Molecular Cloning and Nucleotide Sequence of the Cyclomaltodextrin Glucantransferase Gene from the Alkalophilic *Bacillus* sp. Strain No. 38–2" is an English language reference.
Proceedings of the 4th International Symposium on Cyclodextrins (1988), pp. 87–92, G. Schmid et al. "Selective Complexing Agents for the Production of γ–Cyclodextrin" is an English language reference.
Appl. Microbiol. Biotechnol. (1987) 26, pp. 149–153, Kenji Kimura et al. "Molecular Cloning of the β–Cyclodextrin Synthetase Gene form an alkalophilic *Bacillus* and its expression in *Escherichia coli* and *Bacillus subtilis*" is an English language literature.
Proceedings of the 4th International Symposium on Cyclodextrins (1988), pp. 71–76, G. Schmid et al., "Cloning and Nucleotide Sequence of a Cyclodextrin Glycosyltransferase (List continued on next page.)

*Primary Examiner*—Robert A. Wax
*Assistant Examiner*—Keith D. Hendricks
*Attorney, Agent, or Firm*—Collard & Roe

[57] ABSTRACT

A cyclodextrin glycosyltransferase (CGTase) which, in the conversion of starch or starch-like substrates to CD, produces γ-CD in an increased amount, and whose protein sequence, in the region between amino acid position 180 and amino acid position 240, contains the amino acid sequence (SEQ ID NO: 1), where position 1 of the protein sequence is the beginning of the signal peptide of the CGTase and Xxx denotes a natural amino acid.

8 Claims, No Drawings

OTHER PUBLICATIONS

Gene from the Alkalophilic Bacillus 1—1" is an English language reference.

Agric. Biol. Chem. (1986), 50, pp. 2161–2162, Takashi Kato and Koki Horikoshi "Cloning and Expression of the *Bacillus subtilis* No. 313 γ–Cyclodextrin Forming CGTase Gene in *Escherichia coli*" is an English language reference.

Journal of Fermentation and Bioengineering, vol. 70, No. 3, 150–154, 1990, Yoshito Fujita et al., "Purification and Properties of Cyclodextrin Glycosyltransferase from Bacillus sp. AL–6" is an English language reference.

Journal of Mol. Biol. (1991), 217, pp. 737–750, Claudio Klein and Georg E. Schulz, "Structure of Cyclodextrin Glycosyltransferase Refined at 2.0 Å Resolution" is an English language reference.

Biochemistry (1992), 31, pp. 8740–8746, Claudio Klein et al., "Catalytic Center of Cyclodextrin Glycosyltransferase Derived from x–ray Structure Analysis Combined with Site–Directed Mutagenesis" is an English language reference.

J. H. Miller in (1972) Experiments in Molecular Genetics, Spring Harbor Laboratory, Cold SpriColdarbor, New York, is an English language reference.

Sanger et al. in Proc. Natl. Acad. Sci. USA, vol. 74, No. 12, pp. 5463–5467, Dec. 1977, "DNA sequencing with chain–terminating inhibotors" is an English language reference.

BioTechniques (1992) 13 (3), pp. 342–346, Bio Feedback, "Site Specific Mutagenesis of Almost Any Plasmid Using a PCR–Based Version of Unique Site" is an English language reference.

Technique—A Journal of Methods in Cell and Molecular Biology, vol. 1, No. 1 (Aug.), 1989, pp. 11–15, David W. Leung et al., "A Method for Ramdom Mutagenesis of a Defined DNA Segment using a Modified Polymerase Chain Reaction" is an English language reference.

F. M. Ausubel et al. (1987), Current Protocols in Molecular Biology, Greene Publishing Associates, John Wiley & Sons is an English language reference.

Promega 1992–1993 Catalogue 150, Biological Research Products, "Altered Sites in vitro Mutagenesis System" is an English language reference.

Ann. Rev. Genet. 1985, 19: pp. 423–462, Michael Smith, "In Vitro Mutagenesis" is an English language reference.

Journal of Fermentation and Bioengineering (1990), 70 (3), pp. 190–192, Kenji Tomita et al. "Some Factors Affecting the Formation of γ–Cyclodextrin Using Cyclodextrin Glycosyltransferase from Bacillus sp. AL–6" is an English language reference.

F. M. Ausubel in "Current Protocols in Molecular Biology", (1987) vol. 1; Greene Publishing Associates & Wiley—Interscience, New York is an English language reference.

T. Maniatis et al., Molecular Cloning, A Laboratory Manual, Cold Spring Harbor Laboratory (1982), New York, "Introduction of Plasmid and Bacteriophase γ–DNA into *Escherichia coli*" is an English language reference.

T. Maniatis et al., Molecular Cloning, A Laboratory Manual, Cold Spring Harbor Laboratory (1982), New York, pp. 86–92, "Large Scale Isolation of Plasmid DNA" is an English language reference.

Nucl. Acids. Res. (1986) 14, pp. 9679–9698, K. L. Nakamaye et al., "Inhibition of restriction endonuclease Nci I cleavage by phosphorothioate groups and its application to oligonucleotide–directed mutagenesis" is an English language reference.

Nucleic Acids Research, vol. 16, No. 3, 1988, J. R. Sayers et al. "5'–3'Exonucleases in phosphorothioate–based oligonucleotide—directed mutagenesis" is an English language reference.

T. Maniatis et al., Molecular Cloning, A Laboratory Manual, Cold Spring Harbor Laboratory (1982), New York, "Media and Antibiotics" is an English language reference.

Eur. J. Biochem. 191, pp. 177–185 (1990), FEBS 1990, A. Candussio et al. "Biochemical and Genetic Analysis of a Maltopentaose–producing amylase from an alkaliphilic Gram–positive bacterium" is an English language reference.

Mattsson et al., Applied Biochemistry & Biotechnol., vol. 30, 1991, pp. 17–28.

Sin et al., Appl. Microbiol. Biotechnol., 1991, vol. 35, 600–605.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Asn Leu Xaa Asp
1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Asn Leu Trp Asp
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Asn Leu Ser Asp
1

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Tyr Lys Asn Leu Tyr Asp Leu Ala Asp
1                5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Tyr  Arg  Asn  Leu  Tyr  Asp  Leu  Ala  Asp
1                   5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Tyr  Arg  Asn  Leu  Tyr  Asp  Leu  Ala  Ser
1                   5
```

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:7:

```
ATT  TAT  CGA  AAT  CTT  TGG  GAT  TTA  GCT  AGT  CTA                    33
```

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:8:

```
ATT  TAT  CGA  AAT  CTT  NNN  GAT  TTA  GCT  AGT  CTA                    33
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:9:

```
ATT  TAC  AGA  AAC  TTA  TGG  GAT  CTG  GCA  GAC  TAT                    33
```

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:10:

```
ATC  TAC  AAA  AAC  CTG  TGG  GAC  CTG  GCC  GAC  TTC                    33
```

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:11:

ATC TAC AAA AAC CTG TCT GAC CTG GCC GAC TTC    33

MODIFIED CYCLODEXTRIN GLYCOSYLTRANSFERASES FOR PRODUCING γ-CYCLODEXTRINS

BACKGROUND OF THE INVENTION

1. Field of the Invention

The present invention relates to cyclodextrin glycosyltransferases (CGTases) EC 2.4.1.19 for producing γ-cyclodextrin, to processes for their preparation, and to their use.

2. The Prior Art

As a rule, cyclodextrins are prepared from starch or starch-like substrates. The starch is converted enzymically by CGTases into cyclodextrin (CD). Irrespective of the CGTase used for the reaction, the starch is, for thermodynamic reasons, converted mainly into β-CD if the reaction is carried out until the thermodynamic equilibrium is reached (maximum CD yield). However, in the initial phase, at the beginning of the starch-conversion reaction, the enzymes used for the conversion differ in the composition of the mixture of primary products. A distinction is made between α-, β- or γ-CGTases in dependence on the main product, α-, β- or γ-CD, which is formed by the enzyme in this initial phase.

Hitherto, those enzymes which are suitable for the industrial production of CD, and have already been used, have been detected exclusively in bacteria. Hitherto, α-CGTases have been identified exclusively in *Bacillus macerans* (J. Bacteriol. (1986) 166, pp. 1118–1122), *Bacillus stearothermophilus* (GB 2169902) and *Klebsiella oxytoca* (Gene (1986) 47, pp. 269–277). β-CGTases have been detected, for example, in *Bacillus circulans* (Appl. Microbiol. Biotechnol. (1990) 34, pp. 229–230), *Bacillus megaterium* (U.S. Pat. No. 3,812,011), *Bacillus ohbensis* (JP 74124285), *Micrococcus sp. (EP* 0017242) and in *alkalophilic bacilli* which have not been exactly classified taxonomically, such as *Bacillus sp.* 38-2 (J. Gen. Microbiol. (1988) 134, pp. 97–105), 17-1 (Proceedings of the 4th International Symposium on Cyclodextrins (1988), pp. 87–92, 1011 (Appl. Microbiol. Biotechnol. (1987) 26, pp. 149–153), and 1-1 (Proceedings of the 4th International Symposium on Cyclodextrins (1988), pp. 71–76. Enzymes having an initially high γ-CD-forming activity have been described in *Bacillus subtilis* 313 (Agric. Biol. Chem. (1986), 50, pp. 2161–2162), *Bacillus sp.* A1-6 (J. Ferment. Bioeng. (1990) 70 (3), pp. 150–154), and *Bacillus sp.* 290-3 (Proceedings of the 4th International Symposium on Cyclodextrins (1988), pp. 87–92).

The three-dimensional structure of the β-CGTase from *Bacillus circulans* was elucidated by X-ray structural analysis (J. Mol. Biol. (1991) 217, pp. 737–750). It was possible to deduce from this structure which amino acid residues might be able to directly participate in the construction of the substrate binding site and of the active center of this CGTase, but not which amino acid residues determine the product specificity of this CGTase (Biochemistry (1992) 31, pp. 8740–8746).

Since the CGTases used in the industrial preparation of cyclodextrins always afford mixtures composed of several cyclodextrins when converting starch into cyclodextrins, various processes have been developed for isolating pure cyclodextrins (α, β or γ):

defined CD's can be separated chromatographically from the product mixtures, e.g., on the basis of their differences in molecular weight (described, for example, in U.S. Pat. No. 4,808,232);

when converting starch enzymically into cyclodextrins, complex-forming agents are added which only react with one defined CD, thereby, for example, forming an insoluble complex which can be physically separated out of the reaction mixture. Subsequently, the complex is resolved and the homogeneous CD isolated (described, for example, in EP 0291067);

by means of adding an organic solvent, such as, for example, ethanol, to the reaction mixture, the product composition can be shifted in the direction of γ-CD when a γ-CGTase is used (J. Ferm. Bioeng. (1990) 70 (3), pp. 150–154).

In each of the processes, those CGTases are optimally used which have as high an initial product-formation preference as possible for the CD which is to be prepared in pure form.

The specificity of the β- and γ-CGTases known hitherto is adequate for the industrial production of the corresponding cyclodextrins. By contrast, none of the known γ-CGTases possesses product specificity permitting a comparable production of γ-CD.

In order to prepare γ-CD, therefore, it was proposed in JP 03053892 to convert α- and/or γ-cyclodextrins enzymically into γ-CD by adding the γ-CD-specific complex-forming agent glycosylglycyrrhizin, maltose and a CGTase.

SUMMARY OF THE INVENTION

It is an object of the present invention to provide cyclodextrin glycosyltransferases (CGTases) which, in the conversion of starch or starch-like substrates to CD, produce γ-CD in increased amounts.

A further object of the invention is to provide processes for preparing the CGTases.

A further object of the invention is to provide processes for producing 7-CD with the aid of the CGTases.

The object of the invention is achieved by CGTases whose protein sequence, in the region between amino acid position 180 and amino acid position 240, contains the amino acid sequence (SEQ ID NO: 1), where position 1 of the protein sequence is the beginning of the signal peptide of the CGTase and Xxx denotes a natural amino acid other than Tyr.

Preferably, the CGTases according to the invention contain the amino acid sequence (SEQ ID NO: 2) or (SEQ ID NO: 3) in the region between amino acid position 180 and amino acid position 240 of their protein sequence, where position 1 of the protein sequence is the beginning of the signal peptide of the CGTase.

Particularly preferably, the CGTases according to the invention contain the sequence motif (SEQ ID NO: 2) in the region between amino acid position 180 and amino acid position 240 of their protein sequence, where position 1 of the protein sequence is the beginning of the signal peptide of the CGTase.

When converting starch or starch-like substrates, the CGTases according to the invention produce CD's in a product distribution in which the quotient of γ-CD and the sum of α-CD and γ-CD is greater than the quotient of these products which is achieved when converting starch with the respective, unaltered starting enzyme.

In this context, starting enzyme is understood to mean the CGTase which was used for preparing the CGTase according to the invention. The CGTases according to the invention thus possess, unexpectedly, a higher specificity for γ-CD than that of the starting enzymes used for their preparation.

Examples of CGTases according to the invention are CGTases which are obtained from the CGTases listed in Table 1 by replacing the Tyr which is underlined in each case by another natural amino acid. CGTases are preferred in which the Tyr is replaced by Trp or Ser. CGTases are particularly preferred in which the Tyr is replaced by Trp.

TABLE 1

| CGTase type | From strain | Position | Amino acid sequence |
|---|---|---|---|
| β | B.circulans | 225 | SEQ ID NO: 4 |
| β | B.sp. 1-1 | 213 | SEQ ID NO: 5 |
| β | B.ohbensis | 213 | SEQ ID NO: 5 |
| β | B.subtilis | 218 | SEQ ID NO: 4 |
| γ | B.sp. 290-3 | 207 | SEQ ID NO: 6 |

The list in Table 1 shows, for some CGTases by way of example, the amino acid sequence region which is generally present in β- and γ-CGTases and the Tyr within this sequence region which is relevant for modifying the product specificity. In Table 1, the number of the first amino acid of the amino acid sequence reproduced in each case is designated as the position, with the first amino acid of the signal peptide of the relevant CGTase sequence being counted as position 1. The corresponding sequence region in all β- and γ-CGTases can be found by generally known standard processes. Using likewise-known standard processes, such as those set out by way of example in the present application, enzymes according to the invention can thus be prepared from any β- or γ-CGTases whatsoever by mutagenizing the Tyr in accordance with the invention in such CGTases.

A further object of the invention is achieved by a process in which the DNA sequence of a gene encoding a β- or γ-CGTases is mutated by means of mutagenesis methods which are known per se such that the Tyr situated in the region between amino acid positions 180 and 240 in the sequence motif (SEQ ID NO: 2) of the β- or γ-CGTase employed is thereby replaced in the mutated CGTase by another natural amino acid.

All γ- and β-CGTases are suitable for preparing the CGTases according to the invention. The gene encoding a CGTase is isolated by known processes and the mutation according to the invention is introduced into the gene of the CGTase by "in-vivo" or "in-vitro" mutagenesis processes.

"In-vivo" mutagenesis processes are understood to mean, in particular, those methods in which microorganisms, which chromosomally and/or episomally harbor a gene encoding a CGTase, are mutagenized non-specifically with a mutagen, such as, for example, UV light, nitrosoguanidine or ethyl methylsulfonate. Such a process has been described, for example, by J. H. Miller in (172) Experiments in Molecular Genetics, Cold Spring Harbor Laboratory, Cold Spring Harbor, N.Y.

Subsequently, known methods such as, for example, that of sequence analysis by the chain-termination method described by Sanger et al. in PNAS 74 (1977) 5463-5467, are used to identify mutants in which at least the codon of the CGTase gene which encodes the tyrosine which is homologous to Tyr 229 of the CGTase from *Bacillus circulans* is replaced by a codon which encodes another natural amino acid residue, preferably a serine or tryptophane residue, particularly preferably a tryptophane residue.

Within the meaning of the invention, codons which are homologous to Tyr 229 of the CGTase from *Bacillus circulans* are understood to mean those Tyr-encoding codons of other CGTase genes, which codons encode the Tyr which is underlined in Table 1 in the amino acid sequence motif presented in this table.

Within the meaning of the invention, "in-vitro" mutagenesis methods are understood to mean those methods in which an isolated CGTase gene, or a fragment of a CGTase gene, is modified in a way and manner known per se such that a gene is produced which encodes a CGTase enzyme in which at least the amino acid residue which is homologous to Tyr 229 in the CGTase from *Bacillus circulans* has been replaced by another amino acid residue, preferably a tryptophane residue or a serine residue, particularly preferably a tryptophane residue.

Examples of processes for "in-vitro" mutagenesis which are known from the state of the art are specific (BioTechniques (1992) 13 (3), pp. 342-346) or unspecific (Technique (1989) 1 (1), pp. 11–15) mutagenesis processes using the "PCR" technique. Processes are also known in which the mutation is introduced into the target gene in a directed manner with the aid of a synthetic oligonucleotide. This can take place either using so-called "single-strand processes" (F. M. Ausubel et al. (1987), Current Protocols in Molecular Biology, Green Publishing Associates), or using "double-strand processes" (Promega 1992–1993 Catalog, 150) or using other processes such as described, for example, in Ann. Rev. Genet. (1985) 19, pp. 423-462.

The use for isolating γ-CD from starch is the main area of application of the CGTase according to the invention possessing elevated γ-CD-forming activity. The CGTases according to the invention can be used for this purpose by means of current preparation processes. Current preparation processes for producing γ-CD, in which the CGTases according to the invention can be employed in place of the CGTases designated in these processes, are described, for example, in:

Journal of Fermentation and Bioengineering (1990) 70 (3), pp. 190–192: The preparation of γ-CD using the β- and γ-CD-forming CGTase from *Bacillus sp.* AL-6 in the presence of ethanol, which effects an amplified production of γ-CD.

JP 87 25,976: The preparation of γ-CD using the γ-CGTase from Bacillus sp. 313.

- EP 291,067: Preparation of γ-CD using the CGTase from *Bacillus macerans*. The product specificity for γ-CD is achieved by adding a complex-forming agent, e.g. cyclohexadec-8-en-1-one.

- DE 40 09 822: Production of γ-CD using the γ-CGTase from *Bacillus sp.* 290-3.

Both in comparison with α-CD and in comparison with β-CD, γ-CD possesses specific advantages which identify it as being the CD which is the only possible one, or that which is best suited, for a series of applications.

As compared with α-CD, which is constructed from six glucose units, the γ-CD, which consists of eight glucose units, possesses a higher degree of hydrophobic cavitation which makes it possible also to complex those foreign molecules which, for steric reasons, cannot be complexed by α-CD.

As compared with β-CD (solubility in water at room temperature: approximately 18.5 g/l), γ-CD possesses a substantially higher solubility (at room temperature: approximately 232.0 g/l) and is thus better suited than β-CD for reactions involving complexing from aqueous solutions. The low toxicity of γ-CD is an additional advantage of γ-CD over β-CD and modified β-CD derivatives. In the animal model, α-CD derivatives and β-CD derivatives are more toxic than γ-CD both in oral administration and in intravenous administration.

Other objects and features of the present invention will become apparent from the following detailed description considered in connection with the accompanying Examples which discloses embodiments of the present invention. It should be understood, however, that the Examples are designed for the purpose of illustration only and not as a definition of the limits of the invention.

DETAILED DESCRIPTION OF PREFERRED EMBODIMENTS

EXAMPLE 1

Mutagenesis of the γ-CGTase from *Bacillus sp.* 290-3 (DSM 5850)

Replacement of the amino acid residue tyrosine at position 211 in the γ-CGTase from *Bacillus sp.* 290-3 (deposited with the Deutsche Sammlung fur Mikroorganismen (German Collection of Microorganisms) in Braunschweig under the number DSM 5850) by another, arbitrary amino acid residue, in particular, however, by a tryptophane or serine residue, is achieved by replacing, in a way and manner known to the person skilled in the art, the base triplet of the CGTase structural gene encoding tyrosine 211 by another base triplet, encoding an arbitrary amino acid residue, preferably, however, a tryptophane residue.

For the mutagenesis, the γ -CGTase gene from *Bacillus sp.* 290-3 was first cloned into the commercially available *E. coli* vector pUC19 (Boehringer, Mannheim). To do this, chromosomal DNA from *Bacillus sp.* 290-3 (Proceedings on the 4th International Symposium on Cyclodextrins (1988) 87–92) was isolated and partially cleaved with the restriction endonuclease Sau 3AI (Boehringer, Mannheim) as described by F. M. Ausubel in Current Protocols in Molecular Biology, vol. 1; Greene Publishing Associates & Wiley—Interscience, New York. Fragments in a size range of between two and five kb were isolated and incubated at 16° C. for 12 hours together with pUC19-DNA which had been linearized with the restriction endonuclease BamHI (Boehringer, Mannheim) and T4 DNA ligase. The ligation mixture was used to transform *E. coli* K 12 cells which had been rendered competent to take up DNA by means of known processes (Maniatis, Molecular Cloning, A Laboratory Manual; Cold Spring Harbor Laboratory (1982), N.Y.). The recombinant plasmid, which carries the gene for the γ-CGTase from *Bacillus sp.* 290-3, was isolated from those *E. coli* cells which, following transformation, formed aureoles of starch degradation on starch-containing indicator plates (Maniatis, Molecular Cloning, A Laboratory Manual; Cold Spring Harbor Laboratory (1982), N.Y., pp. 86–92).

The mutagenesis of this gene was carried out using the "oligonucleotide-directed in-vitro mutagenesis system, version 2.1" which is sold commercially by Amersham (Braunschweig) and is based on a process developed by Eckstein (Nucl. Acids. Res. (1986) 14, pp. 9679–9698 and Nucl. Acids. Res. (1988) 16, pp. 791–802). The mutagenesis was carried out exactly in accordance with the protocol which is enclosed with this mutagenesis system from Amersham. The process is summarized below. Details can be obtained from the protocol of this mutagenesis system.

Using commercially available enzymes, such as restriction endonucleases and T4 DNA ligase (Boehringer, Mannheim), that part of the gene, cloned in pUC19, for the γ-CGTase from *Bacillus sp.* 290-3 which contains the base triplet encoding the amino acid residue tyrosine at position 211 of this CGTase was cloned into the commercially available vector M13 (New England Biolabs). One example of such a fragment is a 0.6 kb-sized PstI/EcoRI fragment. This fragment was cloned in M13 vector which had been cleaved with the restriction endonucleases PstI and EcoRI.

Single-stranded, recombinant M13 DNA (template DNA) was isolated, in accordance with the experimental protocol supplied by Amersham, together with the above-mentioned mutagenesis system, from those *E. Coli* host cells which had taken up the recombinant M13 vector.

Chemically defined mutagenesis oligonucleotides having the desired sequence in each case were synthesized for the actual mutagenesis. Such oligonucleotides are obtainable commercially, for example, from MWG (Ebersberg). The sequence of the mutagenesis oligonucleotide was chosen such that the order of the bases in the mutagenesis oligonucleotide is inversely complementary to that part of the nucleotide sequence of the template DNA which encompasses, in each case by 15 bases upstream and downstream, the base triplet which is contained in the template DNA and encodes the tyrosine residue in position 211 of the γ-CGTase from *Bacillus sp.* 290-3. However, instead of the base triplet encoding tyrosine, the mutagenesis oligonucleotide contains such nucleotides which, after completion of the mutagenesis, lead to the production of γ-CGTase derivatives in which, instead of a tyrosine residue, another amino acid residue is located at the position 211.

The sequences of the two mutagenesis oligonucleotides used are depicted in Table 2.

TABLE 2

5'–(SEQ ID NO; 7)–3'

5'–(SEQ ID NO: 8) –3'

Employment of the upper mutagenesis oligonucleotide depicted in Table 2 led to γ-CGTase derivatives in which the tyrosine residue 211 was replaced with a tryptophane residue.

When the lower mutagenesis oligonucleotide depicted in Table 2, a so-called degenerate or "mixed" oligonucleotide, is used, the base triplet encoding tyrosine 211 can be replaced by any of the 64 possible base triplets apart from the triplets encoding Tyr. This oligonucleotide is therefore suitable for producing γ-CGTase derivatives in which the amino acid residue tyrosine at position 211 is replaced by in each case one of the other natural amino acids.

The mutagenesis oligonucleotides were phosphorylated at the 5' end using T4 polynucleotide kinase and ATP (Amersham). The phosphorylated mutagenesis oligonucleotides were bound to the homologous regions of the template DNA. For this purpose, 5 µg of single-stranded template DNA were incubated with approximately 4 pmol of the phosphorylated mutagenesis oligonucleotide at 70° C. for three minutes and then at 37° C. for 30 minutes. Subsequently, a DNA strand which, with the exception of the position to be mutagenesized, was complementary to the template DNA, was synthesized, with the mutagenesis oligonucleotide bound to the template DNA serving as the start point for the synthesis and the template DNA serving as the template for the de novo synthesis of the mutated DNA strand. The synthesis itself took place at 16° C., over a period of 15 hours, following addition of DNA polymerase Klenow fragment (Amersham), a T4 DNA ligase and a nucleotide mix containing the nucleotides dATP, dGTP and dTTP, and, in place of dCTP, the thionucleotide dCTPαS (Amersham).

Remaining molecules of single-stranded template DNA were removed from this synthesis sample. For this, NaCl was added to the sample, which was then filtered through a nitrocellulose filter (Amersham), which specifically binds single-stranded DNA. The double-stranded hybrid DNA remaining in the filtrate was concentrated and desalted by precipitation with EtOH. Subsequently, the hybrid DNA was incubated, at 37° C. for 90 minutes, in a suitable incubation buffer (Amersham) together with NciI (Amersham), a restriction endonuclease which recognizes the nucleotide sequence CC(G/C)GG but only cleaves native DNA strands and not those which contain the nucleotide analog dCTPeS. This treatment resulted in breaks being introduced only into the nonmutagenized strand (template DNA).

The template DNA was then removed in a 30-minute treatment at 37° C. with exonuclease III (Amersham), an enzyme which degrades DNA strands starting from the free ends. Following thermal inactivation of the exonuclease III (70° C. for 15 minutes), the remaining, single-stranded and mutagenized DNA strand was incubated at 16° C. for 3 hours, together with DNA polymerase I (Amersham), T4 DNA ligase and the nucleotides dATP, dTTP, dCTP and dGTP. This resulted in the mutagenized single-stranded DNA being transformed into a double-strand. After a further EtOH precipitation for purification purposes, the mutagenized DNA can be transformed into competent $E.$ $coli$ K12 cells.

The success of the mutagenesis procedure was checked by analyzing the sequence of the relevant region in the recombinant DNA from five of the clones obtained in the transformation. This sequencing was used to determine the mutation obtained when a degenerate mutagenesis oligonucleotide (Table 2, bottom) was used. The DNA fragment which was originally cloned into M13 for the mutagenesis was excised, using appropriate restriction enzymes, from those vectors in which a mutation was confirmed. In the case of the 0.6 Kb fragment used here, the excision was carried out with PstI and EcoRI.

Subsequently, the corresponding, but unmutagenized, PstI/EcoRI fragment was excised from the pUC19-based expression plasmid for the γ-CGTase $Bacillus\ sp.$ 290-3 and replaced by the mutagenized fragment using T4 DNA ligase.

EXAMPLE 2

Mutagenesis of the β-CGTase from $Bacillus\ sp.$ 1—1

In analogy with the method described in Example 1, the codon of the β-CGTase gene from $Bacillus\ sp.$ 1—1 encoding the tyrosine residue at position 217 of the corresponding CGTase was replaced by a triplet which encodes a tryptophane residue. Table 3 shows the oligonucleotide which was used for this mutagenesis.

TABLE 3

5'- (SEQ ID NO: 9) -3'

EXAMPLE 3

Mutagenesis of the β-CGTase from $Bacillus\ circulans$

In analogy with Example 1, the codon of the β-CGTase gene from $Bacillus\ circulans$ encoding the tyrosine residue at position 229 of the corresponding CGTase was replaced by a triplet which encodes either a tryptophane residue (Table 4, top) or a serine residue (Table 4, bottom). Table 4 shows the oligonucleotides which were used for these mutageneses.

TABLE 4

5'–(SEQ ID NO: 10) –3'
5'–(SEQ ID NO: 11) –3'

EXAMPLE 4

Production of $Bacillus\ sp.$ 290-3 γ-CGTase, and Its Derivatives According to the Invention, in $E.\ coli$ In order to produce Bacillus sp. 290-3 β-CGTase and its derivatives prepared in accordance with Example 1, the pUC19-based expression plasmids described in Example 1 were transformed into a secretory strain of $E.\ coli.$ $E.\ coli$ WCM105 was used as the secretory strain of $E.\ coli.$ This strain was prepared from $E.\ coli$ DS 410 as described in EP 338410.

In order, therefore, to produce $Bacillus\ sp.$ 290-3 γ-CGTase or its derivatives, cells of $E.\ coli$ WCM105 containing suitable CGTase expression plasmids were incubated, at 30° C. for 72 hours, in a shaking water bath (rate of revolution, 250 rpm) in LB medium (Maniatis, Molecular Cloning, a Laboratory Manual; Cold Spring Harbor Laboratory (1982), N.Y.) which contained 10 g/l lactose and 0.1 g/l ampicillin. The cells were then separated off by centrifuging at 5000×g. The cell-free culture supernatant contains the γ-CGTase or its derivatives.

EXAMPLE 5

Production of $Bacillus\ sp.$ 1-1 γ-CGTase, and Its Derivatives According to the Invention, in $E.\ coli$ The production was effected in analogy with Example 4, using the expression plasmids described in Example 2.

EXAMPLE 6

Production of $Bacillus\ circulans$ β-CGTase, and Its Derivatives According to the Invention, in $E.\ coli$ The production was effected in analogy with Example 4, using the expression plasmids described in Example 3.

EXAMPLE 7

Conversion of Starch to Cyclodextrins

The activities of the CGTases were determined by the method described in Eur. J. Biochem. (1990) 191, pp. 177–185.

In each case, 10 units per gram of starch of a CGTase to be tested were incubated, at 45° C. and for a defined time, with a 5% solution of a soluble starch (Merck, Darmstadt) in a buffer consisting of 20 mM Tris/HCl pH 7.2, and 5 mM $CaCl_2$. After the defined time, the reaction was terminated by adding 1.5 parts by volume of methanol. Residual starch which had not reacted was precipitated by incubating at 4° C. for 1 hour and separated by centrifugation (10 min., 12,000×g). The resulting products were determined by HPLC on a Nukleosil 10-$NH_2$ column (Macherey & Nagel, Düren), with defined cyclodextrins or linear maltooligosaccharides (Sigma, Munich) serving as standards.

EXAMPLE 8

Conversion of Starch Using Non-Mutagenesized γ-CGTase from *Bacillus sp.* 290-3 and the Derivative Prepared in Accordance with Example 4

The reactions were carried out as described in Example 7. The quantity of linear maltooligosaccharides (G1–G7) arising was added up. The following results were obtained and are set forth in Table 5.

TABLE 5

| Reaction time in minutes | Conversion of the starch to cyclodextrin and G1–G7 (%) | | | | | |
|---|---|---|---|---|---|---|
| | Non-mutagenesized CGTase | | | Mutagenized CGTase | | |
| | β-CD | γ-CD | G1–G7 | β-CD | γ-CD | G1–G7 |
| 5 | 7.0 | 8.6 | 0.0 | 0.0 | 7.8 | 0.0 |
| 10 | 11.0 | 13.0 | 0.0 | 0.0 | 12.8 | 0.0 |
| 15 | 12.6 | 14.4 | 0.0 | 0.0 | 16.2 | 0.0 |
| 30 | 21.4 | 18.2 | 1.2 | 2.0 | 22.8 | 2.2 |

EXAMPLE 9

Conversion of Starching Using the Non-mutagenized β-CGTase from Bacus circulans and the Derivative Prepared in Accordance with Example 6, in Which Derivative the Tyrosine Residue at at Position 229 was Replaced by a Tryptophane Residue The reactions were carried out as described in Example 7. The following results were obtained and are set forth in Table 6.

TABLE 6

| Reaction time in minutes | Conversion of the starch to cyclodextrin (%) | | | | | |
|---|---|---|---|---|---|---|
| | Non-mutagenesized CGTase | | | Mutagenized CGTase | | |
| | α-CD | β-CD | γ-CD | α-CD | β-CD | γ-CD |
| 1 | 0.0 | 6.4 | 1.2 | 0.0 | 1.0 | 4.4 |
| 2 | 0.0 | 10.6 | 2.0 | 0.0 | 2.0 | 8.0 |
| 3 | 1.6 | 13.5 | 2.6 | 0.0 | 2.8 | 14.6 |
| 4 | 2.6 | 16.4 | 5.2 | 0.0 | 4.8 | 17.2 |
| 5 | 3.2 | 18.2 | 7.0 | 0.0 | 5.8 | 16.4 |
| 6 | 2.6 | 20.0 | 6.6 | 0.0 | 6.2 | 16.0 |
| 7 | 3.4 | 22.2 | 7.6 | 1.0 | 7.4 | 16.4 |
| 8 | 3.8 | 23.0 | 6.4 | 1.2 | 8.4 | 19.8 |
| 9 | 4.4 | 24.6 | 7.0 | 1.8 | 9.6 | 22.0 |
| 10 | 4.6 | 26.2 | 6.0 | 1.8 | 8.2 | 20.8 |

EXAMPLE 10

Conversion of Starch Using the Non-mutagenized γ-CGTase from *Bacillus circulans* and the Derivative Prepared in Accordance with Example 6, in Which Derivative the Tyrosine Residue at Position 229 Was Replaced by a Tryptophane Residue, in the Presence of a γ-CD-Complex-Forming Agent The conversion was carried out as described in Example 7 but with the following modifications:

soluble starch was replaced by potato starch;

1.25 grams of CHDC (cyclohexadecenone) were added per 10 grams of starch.

The following results were obtained and are set forth in Table 7.

TABLE 7

| Reaction time in minutes | Conversion of the starch to cyclodextrin (%) | | | | | |
|---|---|---|---|---|---|---|
| | Non-mutagenesized CGTase | | | Mutagenized CGTase | | |
| | α-CD | β-CD | γ-CD | α-CD | β-CD | γ-CD |
| 1 | 2.3 | 18.0 | 5.4 | 1.4 | 10.5 | 13.7 |
| 2 | 3.2 | 20.0 | 7.2 | 2.2 | 13.8 | 22.2 |
| 3 | 4.4 | 21.8 | 9.5 | 3.4 | 15.8 | 23.7 |
| 4 | n.d. | n.d. | n.d. | 3.5 | 11.2 | 25.5 |
| 5 | 5.4 | 20.9 | 12.8 | 3.5 | 11.5 | 29.0 |
| 6 | 5.8 | 21.1 | 14.6 | n.d. | n.d. | n.d. |
| 7 | 6.4 | 20.6 | 17.0 | 4.7 | 11.0 | 32.0 |

EXAMPLE 11

Conversion of Starch Using the Non-mutagenized β-CGTase from Bacillus circulans and the Derivative Prepared in Accordance with Example 6 (Invention), in Which Derivative the Tyrosine Residue at Position 229 Was Replaced by a Serine Residue The reactions were carried out as described in Example 7. The following results were obtained with a 20 minute incubation and are set forth in Table 8.

TABLE 8

| Reaction time in minutes | Conversion of the starch to cyclodextrin (%) | | | | | |
|---|---|---|---|---|---|---|
| | Non-mutagenesized CGTase | | | Mutagenized CGTase | | |
| | α-CD | β-CD | γ-CD | α-CD | β-CD | γ-CD |
| 20 | 4.3 | 20.1 | 6.6 | 1 | 13 | 13 |

While several embodiments of the present invention have been shown and described, it is to be understood that many changes and modifications may be made thereunto without departing from the spirit and scope of the invention as defined in the appended claims.

What is claimed is:

1. A cyclodextrin glycosyltransferase (CGTase) which, in the conversion of starch or starch-like substrates to cyclodextrin (CD), produces γ-CD in an increased amount over its natural production, comprising a CGTase whose protein sequence, in the region between amino acid position 180 and amino acid position 240, contains the amino acid sequence SEQ ID NO: 1, where position 1 of the CGTase's protein sequence is the beginning of the signal peptide of the CGTase and Xaa of SEQ ID NO: 1 denotes a natural amino acid other than Tyr; and wherein Xaa is selected from the group consisting of Trp and Ser.

2. A CGTase as claimed in claim 1, wherein Xaa is Trp.

3. A CGTase as claimed in claim 1, wherein Xaa is Ser.

4. A process for preparing CGTases such that they produce γ-CD in an increased amount over their natural production, comprising mutating the DNA sequence of a gene encoding a β-CGTase or γ-CGTase by means of mutagenesis which results in replacing the Tyr in the region between amino acid positions 180 and 240 in the sequence motif of amino acids 3 through 6 of SEQ ID NO: 4 of the β-CGTase or γ-CGTase by another natural amino acid.

5. The process as claimed in claim 4, comprising replacing the Tyr situated in the region between amino acid positions 180 and 240 in the sequence motif of amino acids 3 through 6 of SEQ ID NO:4 of the β-CGTase or γ-CGTase by an amino acid selected from the group consisting of Trp and Ser.

6. The process as claimed in claim 5, wherein Tyr is replaced by Trp.

7. The process as claimed in claim 5, wherein Tyr is replaced by Ser.

8. In a method for the conversion of starch or starch-like substrates to cyclodextrin, the improvement comprising utilizing the cyclodextrin glycosyltransferase of claim 1 for producing γ-cyclodextrin.

\* \* \* \* \*